United States Patent [19]

Hansen et al.

[11] Patent Number: 5,328,679
[45] Date of Patent: Jul. 12, 1994

[54] METHODS FOR TECHNETIUM/RHENIUM LABELING OF PROTEINS

[75] Inventors: Hans J. Hansen, Mystic Island; Gary L. Griffiths, Morristown; Anastasia Lentine-Jones, Clinton, all of N.J.

[73] Assignee: Immunomedics, Inc., Warren, N.J.

[21] Appl. No.: 760,466

[22] Filed: Sep. 17, 1991

Related U.S. Application Data

[63] Continuation-in-part of Ser. No. 408,241, Sep. 18, 1989, abandoned, Ser. No. 392,280, Aug. 10, 1989, Pat. No. 5,128,119, Ser. No. 364,373, Jun. 12, 1989, abandoned, and Ser. No. 176,421, Apr. 1, 1988, Pat. No. 5,061,641.

[51] Int. Cl.$^5$ .............. A61K 49/02; A61K 43/00; A61K 39/395; C07K 15/28
[52] U.S. Cl. .................. 424/1.49; 530/391.5; 530/402; 424/153
[58] Field of Search ............ 424/1.1; 530/391.5, 530/402

[56] References Cited

U.S. PATENT DOCUMENTS 3,725,295 4/1973 Eckelman .................. 424/1.1
5,078,985 1/1992 Rhodes .................. 424/1.1

FOREIGN PATENT DOCUMENTS 8807382 10/1988 PCT Int'l Appl. .

Primary Examiner—Richard D. Lovering
Assistant Examiner—John M. Covert
Attorney, Agent, or Firm—Foley & Lardner

[57] ABSTRACT

A method for radiolabeling a protein with a radioisotope of technetium or rhenium is disclosed which comprises the steps of contacting a solution of a protein containing a plurality of adjacent free sulfhydryl groups, or in particular cases, intact protein containing at least one disulfide group, with stannous ions, and then with radiopertechnetate or radioperrhenate, the amount of stannous ion being sufficient to substantially completely reduce the radiopertechnetate or radioperrhenate, and recovering radiolabeled protein.

A rapid and quantitative method for producing a sterile, injectable solution of Tc-99m-labeled monovalent antibody fragment is also disclosed which comprises the step of mixing a sterile solution containing a monovalent antibody fragment having at least one free sulfhydryl group, stannous chloride and excess tartrate, at mildly acidic pH, or a sucrose-stabilized lyophilizate of such solution, with a sterile solution of Tc-99m-pertechnetate, whereby substantially quantitative labeling of the antibody fragment with Tc-99m is effected in about 5 minutes at ambient temperature, the resultant sterile solution of Tc-99m-labeled monovalent antibody fragment being suitable for immediate injection into a patient for scintigraphic imaging.

33 Claims, No Drawings

METHODS FOR TECHNETIUM/RHENIUM LABELING OF PROTEINS

BACKGROUND OF THE INVENTION

This application is a continuation-in-part of Shochat et al., U.S. patent application Ser. No. 07/176,421, filed Apr. 5, 1988 (hereinafter, "the '421 application"), Griffiths U.S. patent application Ser. No. 07/364,373, filed Jun. 12, 1989 (hereinafter, "the '373 application"), Griffiths, U.S. patent application Ser. No. 07/392,280, filed Aug. 10, 1989 (hereinafter, "the '280 application"), and Hansen et al., U.S. patent application Ser. No. 07/408,241, filed Sep. 18, 1989 (hereinafter "the '241 application"), the disclosures of all of which are incorporated herein in their entireties by reference.

The present invention relates to improved and optimized methods for direct labeling of proteins, especially antibodies and/or antibody fragments, with radioisotopes of technetium and rhenium.

The present further invention relates to a method and kit for directly and rapidly radiolabeling a monovalent antibody fragment with technetium-99m (Tc-99m), using one or more pendant sulfhydryl groups as endogenous ligands, and more particularly to a method and kit for radiolabeling Fab or Fab' antibody fragments to prepare a sterile, Tc-99m-labeled antibody fragment solution which is almost immediately ready for injection into a patient for scintigraphic imaging.

The isotope technetium-99m is among the most valuable in diagnostic nuclear medicine due to its ready availability, low cost and favorable radiochemical characteristics. It is used widely as an agent for labeling macromolecules such as monoclonal antibodies and can be bound to the protein in various ways. Early work mainly used the bifunctional chelate approach, i.e., use of a chelator which contained another functional group for linkage to the protein. Various forms of diethylenetriaminepentaacetic acid (DTPA) were used, for example, to bind to the antibody and also to chelate the radiometal ion.

Direct labeling of protein was also tried, using a "pretinning" protocol, requiring severe conditions and long "pretinning" times, but radiolabeling at 100% incorporation was not achieved. Moreover, the presence of extremely high amounts of stannous ion for long periods compromised the immunoreactivity of the antibody. The process also generally necessitated a post-labeling purification column. Attempts to repeat pretinning procedures of others with F(ab')$_2$ antibody fragments were unsatisfactory in achieving Tc-99m labeling.

Other, more recent direct labeling methods have required separate vials, one for antibody and one for stannous ion complexed to a transchelator such as a phosphate and/or phosphonate.

European Patent Application A2/0 237 150, to NeoRx Corp., and PCT Application WO 88/07382, to Centocor Cardiovascular Imaging Partners, L.P., each disclose methods for radiolabeling an antibody or antibody fragment with Tc-99m, but the labeling conditions are not optimized for labeling Fab or Fab' fragments and the disclosed conditions are inconvenient and do not result in quantitative labeling.

The element below technetium in the periodic table, rhenium, has similar chemical properties and might be expected to react in an analogous manner to technetium. There are some 34 isotopes of rhenium and two of them in particular, rhenium-186 (t ½, 90h; gamma 137 keV, beta 1.07, 0.93 MeV) and rhenium-188 (t ½, 17h; gamma 155 keV, beta 2.12 MeV), are prime candidates for radioimmunotherapy using monoclonal antibody approaches. Both isotopes also have gamma emmissions at suitable energies for gamma camera imaging purposes. Rhenium-186 is obtained from reactor facilities by bombardment of enriched rhenium-185 with neutrons, which yields rhenium-186 in a "carrier-added" form containing a large excess of non-radioactive rhenium-185. Rhenium-188 is obtained from a tungsten-188/rhenium-188 generator (Oak Ridge National Laboratory) and can be eluted from the generator in a substantially carrier-free form with little tungsten breakthrough. Also, the energy deposition from this isotope at a high $\Delta=1.63$ g-rad/$\mu$Ci-h is close to another potently energetic potential therapeutic, yttrium-90 ($\Delta=1.99$ g-rad/$\mu$Ci-h) while at the same time the chemical properties of rhenium may make it less of a bone-seeking agent than yttrium (which is often contaminated with strontium-90) and give rise to better tumor-/organ biodistribution and dosimetry.

Although many groups have alluded to the possibility of utilizing rhenium to label antibodies in the same fashion as technetium, little successful work has been published. Low rhenium incorporations are usually seen with antibody-chelate conjugates and there is a general tendency of rhenium to reoxidize back to perrhenate and then dissociate from complexation. Besides, use of the bifunctional chelate approach often requires an organic synthesis with a lengthy series of intermediates to be isolated and purified prior to antibody conjugation.

A need continues to exist for a simple, one-vial method for radiolabeling proteins with radioisotopes of technetium and rhenium.

A need also continues to exist for a direct method for stably radiolabeling Fab and Fab' antibody fragments with Tc-99m within a few minutes to produce an solution which is ready for immediate injection into a patient for scintigraphic imaging.

OBJECTS OF THE INVENTION

One object of the present invention is to readily produce a highly immunoreactive technetium or rhenium radiolabeled antibody or antibody fragment which is stable to loss of label by transchelation or reoxidation.

Another object of the invention is to provide a method for direct radiolabeling of a protein which produces high yields of labeled product with minimal contamination with by-products.

Another object of the invention is to provide a convenient and efficient radiolabeling kit for use in introducing technetium or rhenium radioisotope into an antibody or antibody fragment.

Another object of the present invention to provide a method for direct Tc-99m radiolabeling of a monovalent, e,g,. Fab or Fab', antibody fragment which is rapid and convenient and which results in a labeled fragment ready for direct injection into a patient.

Another object of the invention is to provide an "instant" Tc-99m labeling kit for labeling a Fab or Fab' antibody fragment that is stable to prolonged storage but that can be combined directly with the sterile saline effluent from a Tc-99m generator to produce a sterile solution of radioantibody fragment.

Upon further study of the specification and appended claims, further objects and advantages of this invention will become apparent to those skilled in the art.

SUMMARY OF THE INVENTION

The foregoing objectives are achieved, according to one aspect of the invention, by providing a method for radiolabeling a protein containing a plurality of spatially adjacent free sulfhydryl groups with a radioisotope of technetium or rhenium, comprising the steps of contacting a solution of said protein containing a plurality of spatially adjacent free sulfhydryl groups with stannous ions, and then with radiopertechnetate or radioperrhenate, the amount of stannous ion being in slight excess in the case of technetium and in greater excess in the case of rhenium over that required to substantially completely reduce said radiopertechnetate or radioperrhenate, and recovering radiolabeled protein.

According to another aspect of the invention, there is provided a method for producing a sterile, injectable solution of Tc-99m-labeled monovalent antibody fragment, which comprises the step of mixing:

(1A) a sterile solution containing a unit dose for scintigraphic imaging of a monovalent antibody fragment having at least one free sulfhydryl group, stannous chloride in an amount of about 100–150 $\mu$g Sn per mg of antibody fragment, and about a 30–40-fold molar excess of tartrate over stannous chloride, in about 0.04–0.06 M acetate buffer containing saline, at a pH of 4.5–5.0, or (1B) the lyophilizate of a sterile solution containing a unit dose for scintigraphic imaging of a monovalent antibody fragment having at least one free sulfhydryl group, stannous chloride in an amount of about 100–150 $\mu$g Sn per mg of antibody fragment, and about a 30–40-fold molar excess of tartrate over pH of 4.5–5.0, stannous chloride, in about 0.04–0.06 M acetate buffer containing saline and made about 0.08–0.1 M in sucrose, at a pH of 4.5–5.0, with (2) a sterile solution containing an effective scintigraphic imaging amount of Tc-99m-pertechnetate, whereby substantially quantitative labeling of the antibody fragment with Tc-99m is effected in about 5 minutes at ambient temperature, the resultant sterile solution of Tc-99m-labeled monovalent antibody fragment being suitable for immediate injection into a patient for scintigraphic imaging.

The invention also provides technetium or rhenium radio-labeling kits for effecting the labeling process of the invention, especially for producing Tc-99m and rhenium radiolabeled antibodies and antibody fragments, processes for their production, and improved methods of radioantibody imaging and therapy using antibodies and antibody fragments radioalabeled according to the invention.

DETAILED DESCRIPTION

It has now been found that a protein, in particular an antibody or antibody fragment, having a plurality of spatially adjacent free sulfhydryl groups can selectively bind technetium and rhenium radiometal ions, under mild conditions, to form tight bonds to the sulfhydryl groups that are quite stable in blood and other bodily fluids and tissues. Both the reagents and the conditions in the present method are greatly simplified, but the method is particularly adapted for technetium or rhenium labeling and it is surprisingly and unexpectedly shown that optimal conditions for each label are different.

A first method according to the invention thus broadly comprises the step of contacting a solution of a protein containing a plurality of spatially adjacent free sulfhydryl groups, said solution also containing tin(II) ions, with a solution of Tc-99m-pertechnetate or perrhenate (using a radioisotope of rhenium of therapeutic or imaging utility) ions, whereby a solution of technetium or rhenium radiolabeled protein is obtained. The procedure is simple and practical for the nuclear medicine physician and technologist. Preferred embodiments of the first method include applying the method of the invention to produce radiolabeled antibodies or antibody fragments useful for gamma imaging and radioisotope therapy.

The first labeling method and kit of the invention may be used to bind radioiosotopes of technetium and rhenium to other proteins with the requisite free sulfhydryl groups. Proteins which contain two or more proximal free sulfhydryl groups can be labeled directly. Those which contain disulfide groups, normally linked through a cystine residue, can be treated with a reducing agent to generate the free sulfhydryl groups. This may result in fragmentation of the protein if the disulfide bond links polypeptide chains which are not continuous, or it may merely result in chain separation, possibly involving a change in conformation of the protein if the disulfide bond joins remote segments of a single polypeptide chain. Sulfhydryl groups can be introduced into a polypeptide chain to provide the requisite proximal groups.

Reduction of an antibody or F(ab')$_2$ fragment with known disulfide bond reducing agents, e.g., dithiothreitol, cysteine, mercaptoethanol and the like, gives after a short time, typically less than one hour, including purification, antibody having from 1–10 free sulfhydryl groups by analysis. When labeled with technetium using a reducing agent such as stannous ion under the present conditions, 100% incorporation of Tc-99m to protein is seen together with >95% retention of immunoreactivity.

The methods of the invention are particularly attractive for labeling antibodies and antibody fragments, although proteins such as albumin, drugs, cytokines, enzymes, hormones, immune modulators, receptor proteins and the like may also be labeled. Antibodies contain one or more disulfide bonds which link the heavy chains, as well as disulfide bonds which join light and heavy chains together. The latter disulfide bonds are normally less accessible to disulfide reducing agents and the bonds linking heavy chains can normally be selectively cleaved. The resultant fragments retain their immunospecificity and ability to bind to antigen. It will be understood that reduction of disulfide bonds linking the heavy chains of an immunoglobulin must be effected with care, since the normally less reactive disulfide bonds linking light and heavy chains will eventually be reduced if reducing conditions are too drastic or the reducing agent is left in contact with the fragments for too long a time.

Once reduced, the antibody-SH moieties are quite stable if stored under rigorously oxygen-free conditions. Stability is also increased with storage at lower pH, particularly below pH 6.

It will also be understood that the antibodies or antibody fragments to be radiolabeled can be antibodies or fragments thereof which bind to antigens which include but are not limited to antigens produced by or associated with tumors, infectious lesions, microorganisms, parasites, myocardial infarctions, clots, atherosclerotic plaque, or normal organs or tissues.

By "antibodies and antibody fragments" is meant generally immunoglobulins that specifically bind to antigens to form immune complexes. The terms include conventional IgG, IgA, IgE, IgM, and the like, conventional enzyme digestion products such as F(ab')$_2$ fragments obtained by pepsin digestion of intact immunoglobulins, Fab fragments obtained by papain digestion of intact immunoglobulins, conventional monovalent Fab' and light-heavy chain fragments obtained by disulfide bond cleavage of F(ab')$_2$ fragments and intact antibody, respectively. Cleavage is advantageously effected with thiol reducing agents, e.g., cysteine, mercaptoethanol, dithiothreitol (DTT), glutathione and the like. However, monovalent fragments can also include any fragments retaining the hypervariable, antigen-binding region of an immunoglobulin and having a size similar to or smaller than a Fab' fragment. Products having substantially similar properties to such immunoglobulins and fragments are also included. Such similar proteins include antibody subfragments made by further digestion or manipulation of larger fragments, genetically engineered antibodies and/or fragments, whether single-chain or multiple-chain, and synthetic proteins having an antigen recognition domain which specifically binds to an antigen and otherwise functions in vivo in a substantially analogous fashion to a "classical" immunoglobulin. The only substantive requirement for such a protein to be useful in the first method according to the invention is that it have two or more proximal sulfhydryl groups to serve as chelators for the reduced pertechnetate or reduced perrhenate radiometal ion.

The cleaved F(ab')$_2$ fragment containing at least one free sulfhydryl group, which is useful in a second method according to the invention, will be termed "Fab'-SH" herein. Cleaved F(ab)$_2$ will be termed "Fab-SH" herein.

Reduction of F(ab')$_2$ fragments is preferably effected at pH 5.5–7.5, preferably 6.0–7.0, more preferably 6.4–6.8, and most preferably at about pH 6.6, e.g., in citrate, acetate or phosphate buffer, preferably phosphate-buffered saline, and advantageously under an inert gas atmosphere. It is well known that thiol reduction can result in chain separation of the light and heavy chains of the fragment if care is not taken, and the reaction must be carefully controlled to avoid loss of integrity of the fragment.

Cysteine is preferred for such disulfide reductions and other thiols with similar oxidation potentials to cysteine will also be advantageously used. The ratio of disulfide reducing agent to protein is a function of interchain disulfide bond stabilities and must be optimized for each individual case. Cleavage of F(ab')$_2$ antibody fragments is advantageously effected with 10–30 mM cysteine, preferably about 20 mM, and a protein concentration of about 10 mg/ml.

Reduction of a F(ab')$_2$ fragment with known disulfide bond reducing agents gives after a short time, typically less than one hour, including purification, Fab' typically having 1–3 free sulfhydryl groups by analysis. Sulfhydryl groups can be introduced into an antibody fragment to improve radiometal binding. Use of Traut's Reagent (iminothiolane) for this purpose is not preferred, whereas use of oligopeptides containing several adjacent sulfhydryl groups is efficacious. In particular, use of metallothionein or, preferably, its C-terminal hexapeptide fragment (hereinafter, "MCTP"), is advantageous.

The Fab-SH or Fab'-SH fragments are advantageously then passed through a short sizing gel column which will trap low molecular weight species, including excess reducing agent. Suitable such sizing gel columns include, e.g., dextrans such as Sephadex G-25, G-50 (Pharmacia), Fractogel TSK HW55 (EM Science), polyacrylamides such as P-4, P-6 (BioRad), and the like. Cleavage can be monitored by, e.g., size exclusion HPLC, to adjust conditions so that Fab or Fab' fragments are produced to an optimum extent, while minimizing light-heavy chain cleavage, which is generally less susceptible to disulfide cleavage.

The eluate from the sizing gel column is then stabilized in about 0.03–0.07, preferably about 0.05 M acetate buffer, pH about 4.5, made in about 0.1–0.3, preferably about 0.15 M saline, and preferably purged with an inert gas, e.g. argon. In general, it is advantageous to work with a concentration of antibody fragment of about 0.5–5 mg per ml, preferably about 1–3 mg/ml, of solution.

Much less tin(II) is needed to achieve 100% Tc-99m incorporation than was previously thought. The general amount of tin used for labeling compounds with Tc in most prior art methods is about 100–200 micrograms per milligram protein. However, because of the great binding power of the sterically close SH groups in the first method of the invention and the subnanogram quantities of TcO$_4$ that normally must be reduced to obtain adequate activity for gamma imaging, much less tin(II) can be effectively used. Reduction is effected by stannous ion, generally in aqueous solution. It will be appreciated that stannous ion is readily available as its dihydrate, and also can be generated in situ from tin metal, e.g., foil, granules, powder, turnings and the like, by contact with aqueous acid, e.g., HCl, and is usually added in the form of SnCl$_2$, advantageously in a solution that is also about 0.1 mM in HCl.

In general, in the first method of the invention it is advantageous to work with a concentration of antibody or antibody fragment of about 0.01–10 mg per ml, preferably about 0.1–5 mg/ml, of solution, generally in saline, preferably buffered to a mildly acidic pH of about 4.0–4.5. In such case, the amount of stannous ion needed for reduction of a normal imaging activity of pertechnetate is about 0.1–50 μg/ml, preferably about 0.5–25 μg/ml, in proportion to the amount of protein.

When labeling the foregoing quantity of antibody or antibody fragment, the amount of pertechnetate is generally about 2–50 mCi/mg of antibody or antibody fragment, and the time of reaction is about 0.1–10 min. With the preferred concentrations of protein and stannous ions noted above, the it amount of pertechnetate is preferably about 5–30 mCi/mg, and the time of reaction is preferably about 1–5 min.

Pertechnetate is generally obtained from a commercially available generator, most commonly in the form of NaTcO$_4$, normally in saline solution. Other forms of pertechnetate may be used, with appropriate modification of the procedure, as would be suggested by the supplier of a new form of generator or as would be apparent to the ordinary skilled artisan. Pertechnetate is generally used at an activity of about 0 2–10 mCi/ml in saline, e.g., 0.9% ("physiological") saline, buffered at a pH of about 3–7, preferably 3.5–5.5, more preferably about 4.5–5.0. Suitable buffers include, e.g., acetate, tartrate, citrate, phosphate and the like.

The reduction is normally effected under an inert gas atmosphere, e.g., nitrogen, argon or the like. The reaction temperature is generally maintained at about room temperature, e.g., 18°–25° C.

These conditions routinely result in substantantially quantitative incorporation of the label into the protein in a form which is highly stable to oxidation and resistant to transchelation in saline and serum. For example, it is now possible to consistently label IgG, previously reduced with a thiol-generating reagent, with from 0.5 to 5 micrograms of Sn(II) per milligram of IgG, in essentially quantitative yield. Generally, at least about 95% of the label remains bound to protein after standing overnight at 37° C. in serum. Furthermore the immunoreactivity of this protein is hardly reduced after this serum incubation, showing that the conjugates are still completely viable imaging agents out to at least 24 hours.

At these concentrations, no transchelator such as phosphonate, tartrate, glucoheptonate or other well known Sn(II) chelating agent is required to keep the tin in solution. Sn(II) compounds such as stannous chloride and stannous acetate have been used successfully in these experiments. Other readily available and conventional Sn(II) salts are also effective. There are only three essential ingredients; the reduced antibody, the aqueous stannous ion and the pertechnetate solution.

Under the conditions described hereunder, 100% of Tc-99m incorporation into intact antibody and Fab/Fab' fragments can be readily achieved. In the case of F(ab')$_2$, the labeling conditions result in 100% incorporation of Tc-99m, but also produce a certain amount of radiolabeled Fab' in addition to radiolabeled F(ab')$_2$.

The resultant Tc-99m-radiolabeled antibodies and antibody fragments are suitable for use in scintigraphic imaging of, e.g., tumors, infectious lesions, microorganisms, clots, myocardial infarctions, atherosclerotic plaque, or normal organs and tissues. Such imaging methods are well known in the art. The radioantibody solutions as prepared above are ready at for immediate injection, if done in a properly sterilized, pyrogen-free vial. Also, no blocking of free sulfhydryl groups after technetium binding is necessary for stabilization.

By "reduced pertechnate" or "reduced perrhenate" is meant the species of technetium or rhenium ion formed by stannous ion reduction of pertechnetate or perrhenate and chelated by the thiol group(s). It is generally thought that reduced pertechnetate is in the form of Tc(III) and/or Tc(IV) and/or Tc(V) in such chelates, and that reduced perrhenate is in the form of Re(III) and/or Re(IV) and/or Re(V), but higher or lower oxidation states and/or multiple oxidation states cannot be excluded and are within the scope of the invention.

Rhenium is found just below technetium in the periodic table, has the same outer shell electronic configuration, and therefore might be expected to have very similar chemical properties, especially the behavior of analogous compounds. In fact, rhenium compounds qualitatively behave similarly to technetium compounds insofar as reduction and chelation are concerned but their reaction rates are quite different and they are dissimilar in certain important respects.

The radioisotope Re-186 is attractive for therapy and can also be used for imaging. It has a half-life of about 3.7 days, a high LET beta emission (1.07 MeV) and a convenient gamma emission energy (0.137 MeV). By analogy to technetium, rhenium is produced from perrhenate, and the reduced rhenium ions can bind nonspecifically to protein. Accordingly, a method for Re-186 labeling of proteins, wherein the reduced perrhenate is bound to sulfhydryl groups of a protein molecule such as an antibody, would be advantageous. Re-188 is a generator-produced beta and gamma emitter with a half-life of about 17 hours and is suitable for imaging and therapy. The development of commercial generators for rhenium-188 is currently underway; and in a preferred scenario, carrier-free rhenium-188 is added directly to a vial containing stannous ion and IgG, to produce a rhenium radiolabeled protein which is ready for use in less than two hours. The half-life of rhenium-188, at 17 hours, makes speed of preparation particularly important.

The procedure of the first method of the invention is modified somewhat in the case of rhenium from that used with pertechnetate. In contrast to Tc-99m labeling procedures, perrhenate does not label reduced antibodies when low amounts of stannous ion reducing agent and short reactions times are used. However, by the use of higher amounts of stannous ion, e.g., stannous tartrate, and longer reaction times, thiol-reduced antibodies are successfully labeled with rhenium.

By judicious manipulation of conditions, better than 80% rhenium incorporations into antibody can be achieved in just a few hours, which is particularly important for rhenium-188 with its 17 hour half-life and potential for radiobiologic damage to the antibody. Labeling procedures are simpler than those currently required for iodine-131 radiolabeling and much simpler than what is currently required for labeling antibodies with yttrium-90 and copper-67. The short labeling time ensures retention of antibody immunoreactivity.

Conditions will vary depending upon whether the perrhenate is substantially carrier-free (e.g., generator-produced Re-188) or carrier-added (e.g., reactor-produced Re-186), the latter requiring more perrhenate for equivalent activity, and therefore more stannous ion reducing agent, although not necessarily more protein. This is an aspect not treated in the prior art.

Generally, a protein, preferably an antibody or antibody fragment, containing a plurality of adjacent/proximal sulfhydryl groups, will be used in concentrations reflecting the preferred therapy application of radioisotopes of rhenium. The types of protein that can be labeled and the definitions of antibodies and antibody fragment disclosed for technetium labeling are also valid for rhenium radiolabeling.

Labeling with substantially carrier-free Re-188-NaReO$_4$, the form which would normally be produced from a generator, is advantageously effected with the sulfhydryl-containing protein, e.g., antibody or fragment, at a protein concentration of about 1–20 mg/ml, preferably 10–20 mg/ml, in substantially the same solutions and under substantially the same conditions as pertechnetate. The amount of stannous ion used is generally about 100–10,000 μg/ml, preferably about 500–5,000 μg/ml, and preferably in proportion to the amount of protein. Using the foregoing amounts of protein and stannous ion, it is advantageous to use about 10–500 mCi, preferably about 50–250 mCi of substantially carrier-free Re-188-perrhenate, preferably again in proportion to the amount of protein. The reaction time is advantageously about 1 min to 4 hr, preferably about 15 min to 2 hr. Surprisingly and unexpectedly, the reagent ratios and reactions times that were optimal for pertechnetate labeling were not effective for perrhenate, and vice-versa.

Labeling with carrier-added Re-186-NaReO$_4$, the form which would normally be produced from a reactor and which generally contains about a 100- to 1,000-fold excess of Re-185 as carrier, is advantageously effected with the sulfhydryl-containing protein, e.g., antibody or fragment, at a protein concentration of about 1-20 mg/ml, preferably 10-20 mg/ml, in substantially the same solutions and under substantially the same conditions as for Re-188-perrhenate. However, because of the large amount of carrier, the amount of stannous ion used is generally about 1-1,000 mg/ml, preferably about 5-500 mg/ml, and preferably again in proportion to the amount of protein. Approximately the same activity of rhenium radioisotope and about the same reactions times are used for this isotope.

A short column procedure will normally suffice to remove any unbound rhenium and after this time it is ready for immediate injection, if done in a properly sterilized, pyrogen-free vial. Again, no blocking of free sulfhydryl groups after rhenium labeling is necessary for stabilization.

In a surprising and unexpected development, it has now been shown that proteins containing at least one disulfide group, e.g., intact antibodies (without prior reduction) can be simply and directly radiolabeled with rhenium using a larger amount of stannous ion to concommitantly reduce and bind together the antibody and the rhenium species. The "pretinning" procedures described elsewhere and earlier technetium-IgG labeling procedures gave poor results. Long and/or severe reactions are incompatible with the successful generation of an IgG-rhenium injectible.

In general, the concentration of unreduced protein, e.g., antibody, the reaction times, perrhenate activities and other conditions will be substantially the same as for Re-186 or Re-188 labeling of sulfhydryl-containing proteins, except that a larger amount of stannous ion is used. When the radioisotope in the radioperrhenate is substantially carrier-free Re-188, the concentration of antibody or antibody fragment in the solution is advantageously about 1-20 mg/ml, preferably about 10-20 mg/ml, and the amount of stannous ion is about 500-10,000 µg/ml, preferably about 500-5,000 µg/ml. When the radioisotope in the radioperrhenate is carrier-added Re-186, at the same concentration of antibody or antibody fragment, the amount of stannous ion is about 5-1,000 mg/ml, preferably about 50-500 mg/ml.

In fact, unmodified, unreduced IgG has been taken, placed in a vial with a stannous reductant and successfully labeled with perrhenate in as little as 45 minutes at room temperature. No pretinning is used, but perrhenate is added directly after the antibody and tin are mixed. The key is to have sufficient tin to effect a rapid reduction. A short separatory column, simpler in ease of operation than a typical iodine-131 label purification, gives a pure rhenium-IgG conjugate ready for injection.

Exposure of IgG to the conditions used does not impair its immunoreactivity as measured on an affinity column of bound antigen. It appears that an in situ reduction of protein disulfide groups by the stannous ion accompanies the perrhenate reduction and creates the necessary conditions for protein-metal complex formation. The fact that pertechnetate labels IgG much less favorably under the same conditions suggests this as a particularly novel and efficient route for obtaining rhenium antibodies with minimal manipulation.

Rhenium labeling is effected in substantially the same manner as technetium labeling, with special care being taken to insure the absence of air or oxygen in the system. The rhenium-labeled proteins prepared according to the invention show no sign of the ready reoxidation to perrhenate seen by other workers, indicating that the present method is not only facile but also stable. Coupled with this are the facts that much less IgG manipulation is needed for the present method, that Re-188 is available in a convenient generator format (with a single generator capable of daily use for a period of sixty days or more) and that no problems are encountered with strontium contamination, making rhenium-radiolabeled IgG an attractive therapeutic agent.

Rhenium antibody conjugates produced by these methods have been shown to be very stable, even when exposed in solution to the atmosphere for up to 5 days at least. This long term stability is important in an immunoradiotherapeutic, as is retention of immunoreactivity during labeling procedures, which also has been demonstrated.

It must be recognized that the present approach is quite different from prior art approaches, due to the simplicity, effectiveness, efficiency and lack of major manipulation in the process as well as the stability of the rhenium conjugates. It is again emphasized that the relatively higher amount of tin and longer reaction times are not conducive to efficient pertechnetate labeling but are optimal for perrhenate, whereas the low tin, fast labeling conditions optimal for pertechnetate do not work for perrhenate. In particular, for about 1 mg of antibody, and an imaging activity of Tc-99m, very low tin and 5 min reaction times result in excellent results, whereas for therapy levels of Re-186 or Re-188 label, more than 500 µg/ml stannous ion is desirable, especially if intact antibody is used, and reaction times on the order of close to an hour are effective.

A kit for use in radiolabeling a protein, e.g., a Fab'-SH or F(ab)'$_2$ fragment or an intact antibody, with Tc-99m, using generator-produced pertechnetate, would include, e.g., in separate containers: about 0.01-10 mg per unit dose of an antibody or antibody fragment which specifically binds an antigen associated with a tumor, an infectious lesion, a microorganism, a myocardial infarction, a clot, atherosclerotic plaque, or a normal organ or tissue, and which contains a plurality of adjacent free sulfhydryl groups; about 0.1-50 µg per unit dose of stannous ions; and about 2-50 mCi of Tc-99m pertechnetate per mg of antibody or antibody fragment.

A kit for radiolabeling an antibody or antibody fragment with the Re-188 radioisotope of rhenium would typically include, in separate containers: about 1-20 mg per unit dose of an antibody or antibody fragment which specifically binds an antigen associated with a tumor or an infectious lesion, and which contains a plurality of adjacent free sulfhydryl groups; about 100-10 000 µg per unit dose of stannous ions; and about 10-500 mCi of substantially carrier-free Re-188 perrhenate per mg of antibody or antibody fragment.

A kit for radiolabeling an antibody or antibody fragment with the Re-186 radioisotope of rhenium would typically include, in separate containers: about 1-20 mg per unit dose of an antibody or antibody fragment which specifically binds an antigen associated with a tumor or an infectious lesion, and which contains a plurality of adjacent free sulfhydryl groups; about 1-1,000 mg per unit dose of stannous ions; and about 10-500 mCi of carrier-added Re-186 perrhenate per mg of antibody or antibody fragment.

A kit for labeling unreduced intact antibody with either rhenium isotope would be similar to the foregoing, except for the larger amount of stannous ions generally used to reduce some of the disulfide bonds in the antibody as well as reducing the perrhenate. The proteins in such kits are advantageously frozen or lyophilized, in sterile containers, and under an inert gas atmosphere. The kits are conveniently supplemented with sterile vials of buffers, saline, syringes, filters, columns and the like auxiliaries to facilitate preparation of injectable preparations ready for use by the clinician or technologist.

Additional significantly improved reagents and conditions for a kit and method for "instant" Tc-99m labeling of monovalent, e.g., Fab or Fab', antibody fragments containing at least one and preferably a plurality of spatially adjacent stabilized free sulfhydryl groups, have also been provided. Labeling is effected substantially quantitatively at ambient temperature within about 5 minutes of mixing a solution of antibody fragment with pertechnetate, readily available from commercial generators.

In this second method according to the invention, the stabilized Fab-SH or Fab'-SH fragments are next mixed with stannous ion, preferably stannous chloride, and with a stabilizer for the stannous ions. In the second method of the invention, it can be added in the form of $SnCl_2$, advantageously in a solution that is also about 0.01 N in HCl in a ratio of about 100-150, preferably about 123 μg Sn per mg of fragment. Advantageously, the stannous ion solution is prepared by dissolving $SnCl \cdot 2 H_2O$ in 6 N HCl and diluting the resultant solution with sterile $H_2O$ that has been purged with argon.

A stabilizing agent for the stannous ion is advantageously present in the solution. It is known that ascorbate can improve specific loading of a chelator with reduced pertechnetate and minimize formation of $TcO_2$, when the reducing agent is stannous ion. Other polycarboxylic acids, e.g., tartrate, citrate, phthalate, iminodiacetate, ethylenediaminetetraacetic acid (EDTA), diethylenetriaminepentaacetic acid (DTPA) and the like, can also be used. Although polycarboxylic acids are mentioned, by way of illustration, any of a variety of anionic and/or hydroxylic oxygen-containing species could serve this function, e.g., salicylates, acetylacetonates, hydroxyacids, catechols, glycols and other polyols, e.g., glucoheptonate, and the like. Preferred such stabilizers are ascorbate, citrate and tartrate, more preferably tartrate.

While the precise role of such agents is not known, it appears that they chelate stannous ion and may prevent adventitious reactions and/or promote reduction by stabilization of stannic ions, and they may also chelate—and thereby stabilize—certain oxidation states of reduced pertechnetate, thereby serving as transchelating agents for the transfer of these technetium ions to the presumably more stable chelation with one or more thiol groups and other nearby ligands on the protein. Such agents will be referred to as "stabilizers" herein. The molar ratio of stabilizer to stannous ion is about 30:1-40:1.

A solution of stabilizer, e.g., NaK tartrate, advantageously at a concentration of about 0.1 M, in buffer, preferably sodium or ammonium acetate at a pH of about 5.5, is prepared with sterile $H_2O$ purged with argon. One volume of the $SnCl_2$ solution is mixed with enough of the stabilizer solution to provide a 30-40 molar excess, relative to the stannous ion, and the resultant solution is sterile filtered and purged with argon.

The sterile, stabilized $SnCl_2$ solution is mixed with the sterile Fab'-SH or Fab-SH solution to obtain a final concentration of about 100-150, preferably about 123 μg Sn per mg of fragment. The pH is adjusted, if necessary to about 4.5-4.8.

The solution of fragment and stabilized stannous ion is advantageously metered into sterile vials, e.g., at a unit dosage of about 1.25 mg fragment/vial, and the vials are either stoppered, sealed and stored at low temperature, preferably in liquid nitrogen, or lyophilized. In the latter case, the buffer is advantageously ammonium acetate and the solution is made about 0.09 molar with a sugar such as trehalose or sucrose, preferably sucrose, prior to metering into sterile vials. The material in the vials is then lyophilized, the vacuum is broken with an inert gas, preferably argon, and the vials containing the lyophilizate are stoppered, sealed and stored, optionally in the freezer. The lyophilization conditions are conventional and well known to the ordinary skilled artisan. Both the sealed lyophilizate and the sealed liquid nitrogen stored solution are stable for at least 9 months and retain their capacity to be rapidly and quantitatively labeled with Tc-99m ions upon mixing with pertechnetate.

To label a unit dose of antibody fragment, a vial of liquid nitrogen frozen solution is thawed to room temperature by gentle warming, or a vial of lyphilizate is brought to ambient temperature if necessary, and the seal is broken under inert gas, preferably argon. A sterile saline solution of a suitable imaging quantity of pertechnetate is added to the vial and the contents are mixed. When labeling the foregoing unit dosage quantity of antibody fragment, the amount of pertechnetate is generally about 1-50 mCi/mg of antibody fragment, and the time of reaction is about 0.1-10 min. With the preferred concentrations of protein and stannous ions noted above, the amount of pertechnetate is preferably about 5-15 mCi/mg, and the time of reaction is preferably about 1-5 min. This is effectively an "instant" labeling procedure with respect to the prior art processes which generally required 30 minutes to several hours incubation, in some cases at elevated temperatures and/or with additional purification required.

This process also routinely results in substantantially quantitative incorporation of the label into the antibody fragment in a form which is highly stable to oxidation and resistant to transchelation in saline and serum. When labeled with Tc-99m according to the method of the present invention, 100% incorporation of Tc-99m to Fab' is seen (within the limits of detection of the analytical monitor) together with >95% retention of immunoreactivity. The radioantibody solutions as prepared above are ready for immediate injection, if done in a properly sterilized, pyrogen-free vial. Also, no blocking of free sulfhydryl groups after technetium binding is necessary for stabilization. Furthermore the immunoreactivity of the labeled fragment is hardly reduced after serum incubation for a day, showing that the conjugates are still completely viable imaging agents out to at least 24 hours.

A kit for use in radiolabeling a monovalent antibody fragment, e g., an Fab'-SH or Fab-SH fragment, with Tc-99m, using generator-produced pertechnetate, in accordance with the foregoing method, would typically include about 0.01-10 mg, preferably about 1-2 mg, per unit dose of an antibody fragment which specifically binds an antigen, and which contains at least one but preferably a plurality of adjacent free sulfhydryl groups; about 100–150 μg per mg of fragment of stannous ions, and a 30–40 molar excess, relative to the stannous ions, of a stabilizer such as tartrate. The constituents of the kit are provided in a single, sealed sterile vial, in the form of a solution or a lyophilizate, and are mixed just prior to use with about 2–50 mCi of Tc-99m pertechnetate per mg of antibody or antibody fragment. Normally, the kit is used and/or provided in combination with one or more auxiliary reagents, buffers, filters, vials, columns and the like for effecting the radiolabeling steps.

Variations and modifications of these kits will be readily apparent to the ordinary skilled artisan, as a function of the individual needs of the patient or treatment regimen, as well as of variations in the form in which the radioisotopes may be provided or may become available.

It will also be apparent to one of ordinary skill that the radiolabeled proteins, especially antibodies and antibody fragments, prepared according to the method of the invention, will be suitable, and in fact particularly convenient and efficacious, in methods of non-invasive scintigraphic imaging and for radioantibody therapy of tumors and lesions. In particular, in a method of imaging a tumor, an infectious lesion, a myocardial infarction, a clot, atherosclerotic plaque, or a normal organ or tissue, wherein an antibody or antibody fragment which specifically binds to an antigen produced by or associated with said tumor, infectious lesion, myocardial infarction, clot, atherosclerotic plaque, or normal organ or tissue, and radiolabeled with a pharmaceutically inert radioisotope capable of external detection, is parenterally injected into a human patient and, after a sufficient time for the radiolabeled antibody or antibody fragment to localize and for non-target background to clear, the site or sites of accretion of the radiolabeled antibody or antibody fragment are detected by an external imaging camera, it will be an improvement to use as the radiolabeled antibody or antibody fragment a Tc-99m-labeled antibody or antibody fragment made according to the method of the present invention. Such imaging methods are well known in the art.

Moreover, in a method of radioantibody therapy of a patient suffering from a tumor or an infectious lesion, wherein an antibody or antibody fragment which specifically binds to an antigen produced by or associated with a tumor or an infectious lesion, and radiolabeled with a therapeutically effective radioisotope, is parenterally injected into a human patient suffering from such tumor or infectious lesion, it will represent an improvement to use as the radiolabeled antibody or antibody fragment a rhenium radiolabeled antibody or antibody fragment made according to the method of the present invention, either from pre-reduced or unreduced antibody.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Antibody Reduction

In a typical run, a solution of 5 mg of purified monoclonal anti-CEA IgG (antibody which specifically binds to carcinoembryonic antigen, a marker associated with colorectal cancer) in 1 ml of phosphate-buffered saline (PBS), at a pH adjusted to 6.2–6.6, is made 30–50 millimolar in 2-mercaptoethanol. After standing at room temperature for 30–40 minutes, the sample is purified on an acrylamide column with deoxygenated acetate as buffer. The reduced IgG solution is concentrated to 1–2 mg/ml on Centricon and is analyzed for SH groups per IgG by the Ellman reaction. It is stored sterile filtered at 4° C. for convenience or frozen for greater stability of the SH groups.

EXAMPLE 2

Tc-99m Radiolabeling

In a typical run, a solution containing 125 nanograms of tin(II) is mixed with a solution containing $3.6 \times 10^{-10}$ moles of monoclonal anti-CEA with free sulfhydryl groups, prepared according to Example 1 and having 1.2 SH per IgG by the Ellman reaction, giving a 2.9:1 ratio of tin(II) to IgG. Addition of 2 mCi of technetium-99m as pertechnetate in saline, followed by incubation for 5 minutes at room temperature, gives a 100% incorporation of technetium into the protein as measured by HPLC and less than 1% pertechnetate remaining by ITLC in two different elution buffers. Immunoreactivity is >98% when measured on a CEA column.

EXAMPLE 3

Re-186 Radiolabeling

In a typical run, a solution containing 880 micrograms of tin(II) is mixed with a solution containing 1 mg of monoclonal anti-CEA intact antibody. Addition of $18.9 \times 10^{-11}$ mol rhenium-186, with an activity of 9 million cpm, as perrhenate in saline, followed by incubation for 1 hour at room temperature, gives a 75% incorporation of rhenium into the protein. The labeled antibody is stable to air oxidation and its immunoreactivity is high when measured on a CEA column.

EXAMPLE 4

Re-188 Labeling

In a typical run, 1 mg of anti-CEA Fab'-SH (SH generated by reduction of F(ab')$_2$ with cysteine, mercaptoethanol or dithiothreitol), is placed in an argon atmosphere together with 1 ml of 100 mM tartrate +50 mM acetate buffer and an Sn(II) species containing approximately 123 ug of Tin(II). Then, 20–2000 μl of a perrhenate solution depending on concentration, approximately equivalent to up to $1 \times 10^{-9}$ mol rhenium is added.

After mixing, the reaction is effected in 1 to 6 hours with rhenium incorporations of 60 to 100% seen. The labeled protein is immediately applied to an acrylamide column and eluted with either acetate buffer or saline. The labeled protein elutes with the void volume (approx. 5 ml) and is shown to be 100% protein-bound rhenium by ITLC in saline. The conjugates can be equally well purified by a quick run through a mini-column using a syringe barrel, again to give a 100% protein bound label.

The label is put through filters down as low as 0.05 micron pore size to show lack of aggregate and in all column procedures and filtrations essentially 100% recovery of radioactivity is obtained. Chromatography on HPLC and ITLC shows the radioactivity eluting-/migrating with the protein fraction.

EXAMPLE 5

Preparation of Tc-99m-anti-CEA-Fab'

A. Labeling Kit

The following solutions are prepared.

(I) A solution of 0.075 M $SnCl_2$ is prepared by dissolving 3350 mg SnClK2 $H_2O$ in 1 ml of 6 N HCl and diluting the resultant solution with sterile $H_2O$ that has been purged with argon.

(II) A solution of 0.1 M NaK tartrat in 0.05 M NaAc, at pH 5.5, is prepared with sterile $H_2O$ purged with argon.

(III) One volume of solution I is mixed with 26 volumes of solution II, and the resultant solution is sterile filtered and purged with argon.

A solution of anti-CEA-Fab'-SH, prepared from a murine monoclonal $IgG_1$ antibody that specifically binds to carcinoembryonic antigen (CEA) by pepsin cleavange to an F(ab')$_2$ fragment, is reduced to Fab'-SH with 20 mM cysteine; excess cysteine is removed by gel filtration, and the Fab'-SH is stabilized (2 mg/ml) at pH 4.5 in 0.05 M NaOAc buffer which is 0.15 M in saline; and the resultant solution is sterile filtered and purged with argon.

(V) Mix solution IV with enough of solution III to obtain a final concentration of 123 μg Sn per mg of Fab'-SH, and adjust the pH to 4.5–4.8.

Solution V is filled, under argon, into sterile vials (1.25 mg Fab'-SH per vial), stoppered and crimp-seal, and the vials are stored in liquid nitrogen.

Alternatively, $NH_4OAC$ is used instead of NaOAc, solution V is made 0.09 M with sucrose, the resultant solution is filled, under argon, into sterile vials (1.25 mg Fab'-SH per vial) and lyophilized. The vacuum is broken with argon, and the vials containing the lyophilizate are stoppered and crimp-sealed.

B. Labeled Fragment

A vial of liquid nitrogen stored fragment is gently warmed, or a vial of lyophilizate prepared according to part A above is selected. A sterile solution of 10 mCi of sodium pertechnetate in sterile saline from a generator is injected into the vial of Fab'-SH and stabilized stannous ions and mixed by gentle agitation. Labeling is quantitative in five minutes, and the resultant solution of Tc-99m-labeled fragment is ready for immediate injection into a patient.

EXAMPLE 6

Tumor Imaging

A sterile solution of a unit dose of Tc-99m-labeled anti-CEA-Fab' prepared (with liquid nitrogen stored Fab'-SH solution) according to Example 5 is infused intravenously into a patient with a progressively rising CEA titer, the patient having undergone "curative" surgery for a colon carcinoma three years earlier. Scintigraphic imaging 2 hr postinjection demonstrates antibody fragment localization in the pelvis at the site of removal of the primary tumor. Subsequent surgery confirms the presence of a 1.0×0.5 cm carcinoma that is successfully removed.

EXAMPLE 7

Tumor Imaging

A sterile solution of a unit dose of Tc-99m-labeled anti-CEA-Fab' prepared (from lyophilizate) according to Example 5 is infused intravenously into a patient with a 3×2 cm rectal polyp that has been proven by biopsy to be malignant. Imaging 2 hr postinjection demonstrates localized antibody fragment in the primary tumor, the right lobe of the liver and in the lower lobe of the left lung. Needle biopsy confirms the presence of tumor in both the liver and the lung. The original plan to perform surgery and adjuvant radiation therapy is abandoned and palliative chemotherapy is instituted.

The foregoing examples are merely illustrative and numerous variations and modifications can be effected by one of ordinary skill in the art to adapt the method, kit and uses thereof according to the invention to various usages and conditions without departing from the scope and spirit of the invention.

The broad scope of the invention is defined by the appended claims, and by the penumbra of equivalents thereof.

What is claimed is:

1. A method for radiolabeling a protein with the Tc-99m radioisotope of technetium, comprising the steps of contacting a solution of about 0.1–5 mg/ml of an antibody or antibody fragment containing a plurality of adjacent free sulfhydryl groups with about 0.5–25 μg/ml of stannous ions under an inert gas atmosphere, storage of the reduced antibody or antibody fragment under oxygen-free conditions, and then reacting with Tc-99m-radiopertechnetate, in the absence of a transchelator, and recovering radiolabeled protein.

2. The method of claim 1, wherein said free sulfhydryl groups are produced by partial reduction of whole immunoglobulin or a F(ab')$_2$ fragment thereof with a thiol reagent.

3. The method of claim 1, wherein said free sulfhydryl groups are produced by thiol reduction and cleavage of a F(ab')$_2$ antibody fragment to a Fab' fragment.

4. The method of claim 1, wherein said antibody or antibody fragment specifically binds a tumor marker.

5. The method of claim 1, wherein said antibody or antibody fragment specifically binds an antigen associated with an infectious lesion, microorganism, myocardial infarction, clot, atherosclerotic plaque, or normal organ or tissue.

6. The method of claim 1, wherein the amount of pertechnetate is about 2–50 mCi/mg of antibody or antibody fragment, and the time of reaction is about 0.1–10 min.

7. The method of claim 6, wherein the amount of pertechnetate is about 5–30 mCi/mg, and the time of reaction is about 1–5 min.

8. A kit for radiolabeling an antibody or antibody fragment with the Tc-99m radioisotope of technitium, comprising in separate containers:

about 0.01–10 mg per unit dose of an antibody or antibody fragment which specifically binds an antigen associated with a tumor, an infectious lesion, a microorganism, a myocardial infarction, a clot, atherosclerotic plaque, or a normal organ or tissue, and which contains a plurality of adjacent free sulfhydryl groups;

about 0.1-50 μg per unit dose of stannous ions; and
about 2-50 mCi/mg of antibody or antibody fragment of Tc-99m-pertechnetate;
wherein said kit lacks a transchelator.

9. A method for radiolabeling a protein with substantially carrier-free Re-188 perrhenate, comprising the steps of contacting a solution of about 1-20 mg/ml of an antibody or antibody fragment containing a plurality of adjacent free sulfhydryl groups with about 100-10,000 μg/ml of stannous ions under an inert gas atmosphere, storage of the reduced antibody or antibody fragment under oxygen-free conditions, and then with about 10-500 mCi of substantially carrier-free Re-188, and recovering radiolabeling protein.

10. The method of claim 9, wherein said free sulfhydryl groups are produced by partial reduction of whole immunoglobulin or a F(ab')$_2$ fragment thereof with a thiol reagent.

11. The method of claim 9, wherein said free sulfhydryl groups are produced by thiol reduction and cleavage of a F(ab')$_2$ antibody fragment to a Fab' fragment.

12. The method of claim 9, wherein said antibody or antibody fragment specifically binds a tumor marker.

13. The method of claim 9, wherein said antibody or antibody fragment specifically binds an antigen associated with an infectious lesion, microorganism, myocardial infarction, clot, atherosclerotic plaque, or normal organ or tissue.

14. The method of claim 9, wherein the concentration of antibody or antibody fragment in said solution is about 10-20 mg/ml, and the amount of stannous ion is about 500-5,000 μg/ml.

15. The method of claim 9, wherein the time of reaction is about 1 min-4 hr.

16. The method of claim 15, wherein the amount of perrhenate is about 50-250 mCi, and the time of reaction is about 15 min-2 hr.

17. A method for radiolabeling an intact antibody or a F(ab')$_2$ antibody fragment with a radioisotope of rhenium, comprising the steps of contacting a solution of an intact antibody or a F(ab')$_2$ antibody fragment containing at least one disulfide group and which specifically binds to an antigen produced by or associated with a tumor or infectious lesion, with stannous ions under an inter gas atmosphere, storage of the reduced antibody or antibody fragment under oxygen-free conditions, and then with radioperrhenate, without first subjecting said solution containing said intact antibody or a F(ab')$_2$ antibody fragment and stannous ions to a sizing column, the amount of stannous ion being in excess over that required to substantially completely reduce said radioperrhenate but not sufficient to precipitate from said solution, and recovering radiolabeled protein.

18. The method of claim 17, wherein said antibody or antibody fragment specifically binds a tumor marker.

19. The method of claim 17, wherein said antibody or antibody fragment specifically binds an antigen associated with an infectious lesion.

20. The method of claim 19, wherein the amount of perrhenate is about 10-500 mCi, and the time of reaction is about 1 min-4 hr.

21. The method of claim 20, wherein the amount of perrhenate is about 50-250 mCi, and the time of reaction is about 15 min-2 hr.

22. The method of claim 17, wherein the radioisotope in the radioperrhenate is substantially carrier-free Re-188, the concentration of antibody or antibody fragment in said solution is about 1-20 mg/ml, and the amount of stannous ion is about 500-10,000 μg/ml.

23. The method of claim 22, wherein the concentration of antibody or antibody fragment in said solution is about 10-20 mg/ml, and the amount of stannous ion is about 500-5,000 μg/ml.

24. The method of claim 17, wherein the radioisotope in the radioperrhenate is carrier-added Re-186, the concentration of antibody or antibody fragment in said solution is about 1-20 mg/ml, and the amount of stannous ion is about 5-1,000 mg/ml.

25. The method of claim 24, wherein the concentration of antibody or antibody fragment in said solution is about 10-20 mg/ml, and the amount of stannous ion is about 50-500 mg/ml.

26. The method of claim 24, wherein the amount of perrhenate is about 10-500 mCi, and the time of reaction is about 1 min-4 hr.

27. The method of claim 26, wherein the amount of perrhenate is about 50-250 mCi, and the time of reaction is about 15 min-2 hr.

28. A kit for radiolabeling an antibody or antibody fragment with the Re-188 radioscope of rhenium, comprising in separate containers:
(a) about 1-20 mg per unit dose of an antibody or antibody fragment which specifically binds an antigen associated with a tumor or an infectious lesion, and which contains a plurality of adjacent free sulfhydryl groups, and about 100-10,000 μg per unit dose of stannous ions; and
(b) about 10-500 mCi/mg of antibody or antibody fragment of substantially carrier-free Re-188-perrhenate.

29. A method for radiolabeling a protein with carrier-added Re-186, comprising the steps of contacting a solution of about 1-20 mg/ml of protein containing a plurality of adjacent free sulfhydryl groups with about 1-1,000 mg/ml of stannous ions under an inert gas atmosphere, storage of the reduced protein under oxygen-free conditions, and then with about 10-500 mCi of carrier-added Re-186-perrhenate, and recovering radiolabeled protein.

30. The method of claim 29, wherein the concentration of antibody or antibody fragment in said solution is about 10-20 mg/ml, and the amount of stannous ion is about 5-500 mg/ml.

31. The method of claim 29, wherein the time of reaction is about 1 min-4 hr.

32. The method of claim 31, wherein the amount of perrhenate is about 50-250 mCi, and the time of reaction is about 15 min-2 hr.

33. A kit for radiolabeling an antibody or antibody fragment with the Re-186 radioisotope of rhenium, comprising in separate containers:
(a) about 1-20 mg per unit dose of an antibody or antibody fragment which specifically binds an antigen associated with a tumor or an infectious lesion, and which contains a plurality of adjacent free sulfhydryl groups, and about 1-1,000 mg per unit dose of stannous ions; and
(b) about 10-500 mCi/mg of antibody or antibody fragment of carrier-added Re-186-perrhenate.

* * * * *